(12) United States Patent
Kishi et al.

(10) Patent No.: US 9,878,974 B2
(45) Date of Patent: Jan. 30, 2018

(54) ESTER OF PENTAERYTHRITOL AND ISOTRIDECANOIC ACID USED THEREFOR

(71) Applicant: KH NEOCHEM CO., LTD., Tokyo (JP)

(72) Inventors: Junya Kishi, Yokkaichi (JP); Shinji Tanaka, Tokyo (JP)

(73) Assignee: KH NEOCHEM CO., LTD., Tokyo (JP)

( * ) Notice: Subject to any disclaimer, the term of this patent is extended or adjusted under 35 U.S.C. 154(b) by 0 days.

(21) Appl. No.: 15/315,091

(22) PCT Filed: Feb. 6, 2015

(86) PCT No.: PCT/JP2015/053424
§ 371 (c)(1),
(2) Date: Nov. 30, 2016

(87) PCT Pub. No.: WO2015/182172
PCT Pub. Date: Dec. 3, 2015

(65) Prior Publication Data
US 2017/0204046 A1    Jul. 20, 2017

(30) Foreign Application Priority Data

May 30, 2014 (JP) ................... 2014-113511
Nov. 14, 2014 (JP) ................... 2014-232032

(51) Int. Cl.
| A23D 9/00 | (2006.01) |
| C07C 69/34 | (2006.01) |
| C07C 69/33 | (2006.01) |
| C07C 53/126 | (2006.01) |
| C10M 105/38 | (2006.01) |

(52) U.S. Cl.
CPC ............ C07C 69/34 (2013.01); C07C 53/126 (2013.01); C07C 69/33 (2013.01); C10M 105/38 (2013.01)

(58) Field of Classification Search
CPC .................................................. C07C 69/34
USPC ........................................................ 554/227
See application file for complete search history.

(56) References Cited

U.S. PATENT DOCUMENTS

| 4,912,279 A | 3/1990 | Wilcher et al. |
| 5,177,282 A | 1/1993 | Nierlich et al. |
| 5,710,323 A | 1/1998 | Okuda et al. |
| 6,263,683 B1 | 7/2001 | Tazaki |
| 6,365,783 B1 | 4/2002 | Yokomori et al. |
| 6,395,701 B1 | 5/2002 | Connor et al. |
| 2001/0027655 A1 | 10/2001 | Tazaki |
| 2003/0100469 A1 | 5/2003 | Connor et al. |
| 2003/0236180 A1 | 12/2003 | Connor et al. |
| 2004/0087461 A1 | 5/2004 | Connor et al. |
| 2004/0092418 A1 | 5/2004 | Connor et al. |
| 2004/0092419 A1 | 5/2004 | Connor et al. |
| 2004/0097392 A1 | 5/2004 | Connor et al. |
| 2005/0145823 A1 | 7/2005 | Yamada et al. |
| 2005/0153869 A1 | 7/2005 | Connor et al. |
| 2006/0255313 A1 | 11/2006 | Yamada et al. |
| 2010/0051854 A1 | 3/2010 | Sawada et al. |
| 2012/0172624 A1 | 7/2012 | Grass et al. |
| 2015/0001438 A1 | 1/2015 | Kishi et al. |

FOREIGN PATENT DOCUMENTS

| JP | 61004377 | 2/1986 | |
| JP | 62-1930 | 1/1987 | |
| JP | 63-225328 | 9/1988 | |
| JP | 3-275145 | 12/1991 | |
| JP | 5505806 | 8/1993 | |
| JP | 2726138 | 12/1997 | |
| JP | 2000169869 A | * 6/2000 | |
| JP | 2000169869 A | 6/2000 | |
| JP | 2001520304 A | * 10/2001 | |
| JP | 2001520304 A | 10/2001 | |
| JP | 3847466 | 11/2006 | |
| JP | 2008247993 A | * 10/2008 | |
| JP | 2008247993 A | 10/2008 | |
| JP | 4368454 | 9/2009 | |
| JP | 2012052135 A | 3/2012 | |
| JP | 2012052135 A | * 3/2012 | ............. C09K 5/045 |
| JP | 2012533589 A | 12/2012 | |
| WO | WO-91/15455 A1 | 10/1991 | |
| WO | WO-96/10006 A1 | 4/1996 | |
| WO | WO-2008/117657 A1 | 10/2008 | |
| WO | WO 2008117657 A1 * | 10/2008 | .......... C10M 105/38 |
| WO | WO-2013/115296 A1 | 8/2013 | |
| WO | WO 2013115296 A1 * | 8/2013 | ............. C09K 5/041 |

OTHER PUBLICATIONS

TMasuda et al., "Studies on Alkaline Oxidation of Alcohols", Journal of Oleo Science, Japan Oil Chemists' Society, vol. 19, No. 12, 1970, pp. 1087-1090.*
Masuda et al., "Studies on Alkaline Oxidation of Alcohols", Journal of Oleo Science, Japan Oil Chemists' Society, vol. 19, No. 12, 1970, pp. 1087-1090.
Binran et al., Maruzen Co., Ltd., Japan Oil Chemists' Society, 4th Edition, 2001, 11 pages.
Kodama et al., McMurry Yuki Kagaku (Jo), Organic Chemistry, 4th Edition, Kabushiki Kaisha Tokyo Kagaku Dojin, 1998, 8 pages.
Tribology Sosho 8 Junkatsu Grease to Gosei Junkatsuyu, Kabushiki Kaisha Saiwai Shobo, 1983, 14 pages.

(Continued)

*Primary Examiner* — Deborah D Carr
(74) *Attorney, Agent, or Firm* — Marshall, Gerstein & Borun LLP

(57) ABSTRACT

Provided are an ester of isotridecanoic acid and pentaerythritol, etc., wherein (i) the kinematic viscosity at 40° C. is in the range of 80-140 mm$^2$/sec. and (ii) the number of terminal methyl groups per molecule of isotridecanoic acid in the isotridecanoic acid obtained by $^1$H-NMR measurement is in the range of 2.6-3.4 on average.

7 Claims, No Drawings

(56) References Cited

OTHER PUBLICATIONS

Search Report and Written Opinion in International Application No. PCT/JP2015/053424 dated Mar. 24, 2015, 3 pages.

\* cited by examiner

ESTER OF PENTAERYTHRITOL AND ISOTRIDECANOIC ACID USED THEREFOR

TECHNICAL FIELD

The present invention relates to an ester of pentaerythritol and so forth used in industrial lubricants and the like.

BACKGROUND ART

Due to recent hard use conditions, lubricant base oils and grease base oils which are used in lubricant compositions and grease compositions such as an engine oil, a gear oil, and a refrigerating machine oil have been required to have enhanced durabilities such as thermal stability, chemical stability, anti-wear properties, and fatigue resistance. Further, energy saving, low-temperature fluidity, low volatility in a high-temperature range, and so forth have also been required. In this respect, the chemical stability includes oxidation stability, hydrolysis stability, oxidation-hydrolysis stability, and the like.

International Publication No. WO2008/117657 describes a refrigerating machine oil characterized by containing an ester of a polyhydric alcohol and fatty acids in which a proportion of branched fatty acids having 10 to 13 carbon atoms is 50 mol % or more.

Published Japanese Translation of PCT International Application No. Hei 5-505806 states that an ester of a C10 to C15 branched aliphatic carboxylic acid containing on average more than one branch per molecule in which no more than 20% of the branching is on the 2 carbon, and an aliphatic alcohol having at least three hydroxyl groups is useful for cutting fluids, hydraulic fluids, and the like.

However, these literatures do not desclose or suggest the characteristics such as low-temperature fluidity, oxidation stability, and low volatility required for lubricant base oils and grease base oils.

SUMMARY OF INVENTION

An object of the present invention is to provide an ester of pentaerythritol and so forth used in industrial lubricants and the like having excellent properties such as low-temperature fluidity, oxidation stability, and low volatility.

The present inventors have conducted earnest studies in order to achieve the above object. As a result, the inventors have found out that the object is achieved by a ester of pentaerythritol with particular isotridecanoic acid. Specifically, the present invention provides the following [1] to [5].

[1] An ester of pentaerythritol with isotridecanoic acid, wherein
(i) the ester of pentaerythritol has a kinematic viscosity at 40° C. within a range of 80 to 140 mm$^2$/s, and
(ii) the number of terminal methyl groups per isotridecanoic acid molecule in the isotridecanoic acid determined by $^1$H-NMR measurement is within a range of 2.6 to 3.4 on average.

[2] The ester of pentaerythritol according to [1], wherein a proportion of tertiary carbon atoms in total constituent carbon atoms of the isotridecanoic acid determined by $^{13}$C-NMR measurement is within a range of more than 10% by mass to 20% by mass or less.

[3] The ester of pentaerythritol according to [1] or [2], wherein the isotridecanoic acid is isotridecanoic acid derived from a product obtained by hydroformylating a butene trimer in presence of a cobalt catalyst and a gas mixture of hydrogen and carbon monoxide.

[4] The ester of pentaerythritol according to [1] or [2], wherein the isotridecanoic acid is isotridecanoic acid derived from a product obtained by hydroformylating a butene trimer in presence of a rhodium catalyst and a gas mixture of hydrogen and carbon monoxide.

[5] An isotridecanoic acid wherein
the number of terminal methyl groups per molecule of the acid determined by $^1$H-NMR measurement is within a range of 2.6 to 3.4 on average, and
a proportion of tertiary carbon atoms in total constituent carbon atoms of the acid determined by $^{13}$C-NMR measurement is within a range of more than 10% by mass to 20% by mass or less.

The present invention makes it possible to provide an ester of pentaerythritol and so forth used in industrial lubricants and the like having excellent properties such as low-temperature fluidity, oxidation stability, and low volatility.

DESCRIPTION OF EMBODIMENTS

An ester of pentaerythritol of the present invention (hereinafter referred to as ester of the present invention) is an ester of pentaerythritol with isotridecanoic acid, wherein (i) the ester has a kinematic viscosity at 40° C. within a range of 80 to 140 mm$^2$/s, and (ii) the number of terminal methyl groups per isotridecanoic acid molecule in the isotridecanoic acid determined by $^1$H-NMR measurement is within a range of 2.6 to 3.4 on average. Note that the ester of the present invention is a complete ester in which all four hydroxyl groups of pentaerythritol are esterified, but may contain a partial ester as an impurity in which some of the hydroxyl groups of pentaerythritol are not esterified and remain in the form of hydroxyl group.

The isotridecanoic acid constituting the ester of the present invention is a mixture of branched isomers of tridecanoic acid. It has been found out that using the mixture of branched isomers of tridecanoic acid, that is, isotridecanoic acid in which the number of terminal methyl groups per isotridecanoic acid molecule is within a particular range, as the carboxylic acid constituting the ester of the present invention makes it possible to provide an ester suitable as industrial lubricants and the like.

The number of terminal methyl groups per molecule of the isotridecanoic acid constituting the ester of the present invention is calculated as an average value according to the following formula 1 using the $^1$H-NMR measurement result of the isotridecanoic acid. The $^1$H-NMR measurement method is described in the section of Examples.

The number of terminal methyl groups per isotridecanoic acid molecule=(a sum of integrated values of peaks assigned to hydrogens of the methyl groups/a sum of integrated values of peaks assigned to hydrogens of hydrocarbon groups)×25/3   (formula 1)

Here, the peaks assigned to hydrogens of the methyl groups are peaks which appear in a range from 0.5 ppm to a chemical shift (ppm) at a minimum value of peaks which appear within a range of 0.9 to 1.1 ppm. The degree of branching of the hydrocarbon group can be grasped from the number of terminal methyl groups obtained by the formula 1.

The number of terminal methyl groups per isotridecanoic acid molecule constituting the ester of the present invention is within a range of 2.6 to 3.4 on average, and preferably within a range of 2.7 to 3.2 on average from the viewpoints that the ester of the present invention has a low-temperature fluidity, an oxidation stability, and a low volatility.

In the present invention, the proportion of tertiary carbon atoms in total constituent carbon atoms of the isotridecanoic acid is not particularly limited. Nevertheless, from the viewpoints that the ester of the present invention has a low-temperature fluidity, an oxidation stability, and a low volatility, the proportion is preferably within a range of more than 10% by mass to 20% by mass or less, more preferably within a range of more than 10% by mass to 16% by mass or less, and furthermore preferably within a range of 12 to 14% by mass.

The proportion of tertiary carbon atoms is calculated according to the following formula 2 using the quantitative $^{13}$C-NMR spectrum (by the inverse gated decoupling technique) of the isotridecanoic acid. The $^{13}$C-NMR measurement method is conducted as described in the section of Examples.

The proportion [% by mass] of tertiary carbon atoms in total constituent carbon atoms of the isotridecanoic acid=(a sum of integrated values of peaks assigned to the tertiary carbon atoms/a sum of integrated values of all peaks)×100  (formula 2)

Here, the peaks assigned to the tertiary carbon atoms are assigned according to the following procedure by using the DEPT technique of $^{13}$C-NMR.

1) Conduct DEPT-90 experiment and DEPT-135 measurement on isotridecanoic acid.

2) Adjust phases such that all the peaks in the DEPT-90 spectrum are oriented in the same direction as primary and tertiary peaks in the DEPT-135 spectrum.

3) Adjust the heights of the spectra such that the maximum peak in the DEPT-90 spectrum has the same intensity as the corresponding peak in the DEPT-135 spectrum.

4) Compare peak intensities between the DEPT-90 spectrum and the DEPT-135 spectrum, and when a peak intensity in the DEPT-135 spectrum is 50% or more of a peak intensity in the DEPT-90 spectrum, assign the peak as a peak of a tertiary carbon atom.

In the present invention, the proportion of branching at the α carbon (carbon atom at the α-position of the carboxyl group) of the isotridecanoic acid is not particularly limited, but is preferably within a range of 15 to 70% by mass, and more preferably within a range of 15 to 60% by mass from the viewpoints that the ester of the present invention has a low-temperature fluidity, an oxidation stability, and a low volatility.

The proportion of branching at the α carbon can be calculated according to the following formula 3 using the quantitative $^{13}$C-NMR spectrum of the isotridecanoic acid. The $^{13}$C-NMR measurement method is conducted as described in the section of Examples.

The proportion [% by mass] of branching at the α carbon=100×(a sum of integrated values of peaks at 182.0 ppm to 186.0 ppm/a sum of integrated values of peaks at 179.0 ppm to 186.0 ppm)  (formula 3)

Here, the peaks at 179.0 ppm to 186.0 ppm are peaks corresponding to the carboxyl group of the isotridecanoic acid. Particularly, in a case where there are one or more branchings at the α carbon, the peaks of the carboxyl group appear at 182.0 ppm to 186.0 ppm, so that the proportion [% by mass] of branching at the α carbon can be calculated according to the formula 3.

From the viewpoints that the ester of the present invention has a low-temperature fluidity, an oxidation stability, and a low volatility, the most preferable embodiment of the isotridecanoic acid constituting the ester of the present invention includes isotridecanoic acid wherein the number of terminal methyl groups per isotridecanoic acid molecule determined by $^{1}$H-NMR measurement is within a range of 2.6 to 3.4 on average, and the proportion of tertiary carbon atoms in total constituent carbon atoms of the isotridecanoic acid determined by $^{13}$C-NMR measurement is within a range of more than 10% by mass to 20% by mass or less.

The isotridecanoic acid constituting the ester of the present invention can be synthesized, for example, by the following methods (i) to (iv):

(i) a method in which tridecanal is isolated by distillation from a mixture of tridecanal and tridecanol obtained by hydroformylating a mixture of branched isomers of dodecene, and the distillate is oxidized by a known method such as oxidation with oxygen;

(ii) a method in which a mixture of tridecanal and tridecanol obtained by hydroformylating a mixture of branched isomers of dodecene is oxidized by a known method such as oxidation with oxygen, and tridecanoic acid thus formed is isolated by distillation;

(iii) a method in which a mixture of tridecanal and tridecanol obtained by hydroformylating a mixture of branched isomers of dodecene is hydrogenated to convert tridecanal in the mixture into tridecanol, and obtained tridecanol is oxidized; and (iv) a method in which a mixture of branched isomers of dodecene is subjected to the Koch reaction.

The method for hydroformylating a mixture of branched isomers of dodecene described in the methods (i) to (iii) includes a method in which a mixture of branched isomers of dodecene is reacted in the presence of a cobalt catalyst or a rhodium catalyst and a gas mixture of hydrogen and carbon monoxide. Moreover, an example of the method for oxidizing tridecanol described in the method (iii) includes a method in which tridecanol is oxidized in the presence of an alkali according to the method described in "Journal of Oleo Science," issued by the Japan Oil Chemists' Society, 1970, Vol. 19, No. 20, pp. 1087 to 1090, or the like.

The method for hydroformylating a mixture of branched isomers of dodecene in the presence of a cobalt catalyst includes a method in which a mixture of branched isomers of dodecene is hydroformylated in a single stage or multiple stages in the presence of a cobalt catalyst and a gas mixture of hydrogen and carbon monoxide according to a known method, for example, the method described in Japanese Examined Patent Application Publication No. Sho 62-1930, Japanese Patent No. 4368454, or the like. As the conditions of the hydroformylation, for example, the reaction pressure is 5 to 35 MPa, preferably 10 to 30 MPa; the reaction temperature is 120 to 200° C., preferably 140 to 170° C.; and the ratio of hydrogen and carbon monoxide in the gas mixture (hydrogen/carbon monoxide: molar ratio) is 0.8 to 2.0, preferably 1.0 to 1.6. Examples of the cobalt catalyst include cobalt carbonyl complexes such as octacarbonyldicobalt, and the like, organic acid salts of cobalt such as cobalt acetate, cobalt hydroxides, cobalt oxides, and the like. Treating these cobalt catalysts with a gas mixture of hydrogen and carbon monoxide forms hydridotetracarbonylcobalt which is presumably the active species of the hydroformylation.

The method for hydroformylating a mixture of branched isomers of dodecene in the presence of a rhodium catalyst includes a method in which a mixture of branched isomers of dodecene is hydroformylated in a single stage or multiple stages in the presence of a rhodium catalyst and a gas mixture of hydrogen and carbon monoxide according to a known method, for example, the method described in Japanese Patent Application Publication No. Sho 63-225328, Japanese Patent No. 3847466, or the like. As the conditions of the hydroformylation, for example, the reaction pressure is 0.5 to 20 MPa, preferably 0.5 to 10 MPa; the reaction temperature is 50 to 170° C., preferably 90 to 150° C.; and the ratio of hydrogen and carbon monoxide in the gas mixture (hydrogen/carbon monoxide: molar ratio) is 0.8 to 2.0, preferably 1.0 to 1.6. Examples of the rhodium catalyst include rhodium carbonyl complexes such as carbonylhydridotris(triphenylphosphine)rhodium and (acetylacetonato)dicarbonylrhodium, and the like, organic acid salts of rhodium such as rhodium acetate, inorganic acid salts of rhodium such as rhodium nitrate, rhodium oxides, and the like. Treating these rhodium catalysts with a gas mixture of hydrogen and carbon monoxide forms the active species of the hydroformylation. Additionally, it is also possible to advantageously use catalysts obtained by adding a phosphine ligand, a phosphite ligand, or the like to these rhodium catalysts.

The Koch reaction described in the method (iv) includes a method in which a mixture of branched isomers of dodecene is reacted in the presence of a catalyst such as sulfuric acid, phosphoric acid, hydrogen fluoride, or boron trifluoride, carbon monoxide, and water according to a known method, for example, the method described in Japanese Examined Patent Application Publication No. Sho 61-4377, International Publication No. WO96/10006, or the like. As the reaction conditions, for example, the partial pressure of carbon monoxide is 0.1 to 10 MPa, preferably 0.2 to 5 MPa, and the reaction temperature is −40 to 80° C., preferably −20 to 60° C.

Examples of the mixture of branched isomers of dodecene include butene trimers, isobutene trimers, propylene tetramers, mixtures thereof, and the like. Nevertheless, the mixture of branched isomers of dodecene preferably contains a butene trimer or a butene trimer as a main component from the viewpoints that the ester of the present invention has a low-temperature fluidity, an oxidation stability, a low volatility, and so forth. In this respect, the term butene refers to a mixture of 1-butene, 2-butene, and isobutene. The isobutene content in the mixture is preferably less than 30% by mass, and more preferably less than 10% by mass from the viewpoints that the ester of the present invention has a low-temperature fluidity, an oxidation stability, a low volatility, and so forth. Moreover, the butene trimer preferably has an initial boiling point within a range of 185 to 195° C., and preferably has a dry point within a range of 195 to 215° C.

The mixture of branched isomers of dodecene can be produced by a known method, for example, an oligomer of butene, isobutene, or propylene is formed in the presence of a homogeneous catalyst or a heterogeneous catalyst, and then purified by distillation to obtain an olefin distillate having 12 carbon atoms. Examples of the homogeneous catalyst include solubilized nickel complexes and the like. Specific examples of the solubilized nickel complexes include catalysts containing a nickel carboxylate, an alkyl aluminum halide, and an alkylene glycol described in Japanese Examined Patent Application Publication No. Sho 61-26888 or the like, and other similar catalysts. Examples of the heterogeneous catalyst include a fixed bed catalyst containing nickel described in Japanese Patent No. 2726138 or the like, a solid phosphoric acid catalyst described in Japanese Patent Application Publication No. Hei 3-275145 or the like, and other similar catalysts.

In a case where the mixture of branched isomers of dodecene is not a mixture of branched isomers of dodecene containing a butene trimer or a butene trimer as a main component (for example, in a case of a propylene tetramer), the number of terminal methyl groups per molecule of the isotridecanoic acid derived from the mixture of branched isomers of dodecene through the hydroformylation method tends to be outside the range of 2.6 to 3.4 on average. In addition, an ester of pentaerythritol with the isotridecanoic acid tends to have a kinematic viscosity at 40° C. outside the range of 80 to 140 mm$^2$/s.

The number of terminal methyl groups per isotridecanoic acid molecule, the proportion of tertiary carbon atoms in total constituent carbon atoms, and the proportion of branching at the α carbon (carbon atom at the α position of the carboxyl group) are influenced by the number of terminal methyl groups per molecule in the mixture of branched isomers of dodecene, which serves as the raw material, but can also be adjusted depending on the above-described different methods for synthesizing the isotridecanoic acid, as well as the type of the catalyst, the rate of the reaction, the distillation condition, and the like in each production method.

The ester of the present invention can be synthesized, for example, by reacting the isotridecanoic acid and pentaerythritol constituting the ester of the present invention at 120 to 300° C. for 5 to 40 hours.

A catalyst may be used in the reaction. Examples of the catalyst include mineral acids, organic acids, Lewis acids, organometals, solid acids, and the like. Specific examples of the mineral acids include hydrochloric acid, hydrofluoric acid, sulfuric acid, phosphoric acid, nitric acid, and the like. Specific examples of the organic acids include p-toluenesulfonic acid, benzenesulfonic acid, butanesulfonic acid, propanesulfonic acid, ethanesulfonic acid, methanesulfonic acid, and the like. Specific examples of the Lewis acids include boron trifluoride, aluminum chloride, tin tetrachloride, titanium tetrachloride, and the like. Specific examples of the organometals include tetrapropoxytitanium, tetrabutoxytitanium, tetrakis(2-ethylhexyloxy)titanium, and the like. Specific examples of the solid acids include cation-exchange resins and the like. It is preferable to carry out the reaction while removing water formed by the reaction from the reaction mixture.

The amount of the isotridecanoic acid used is preferably 1.1 to 1.4 times larger in terms of moles than the hydroxyl groups of pentaerythritol used.

A solvent may be used in the reaction. Examples of the solvent include hydrocarbon-based solvents such as benzene, toluene, xylene, hexane, heptane, isohexane, isooctane, isononane, and decane, and other similar solvents. In the reaction, unreacted isotridecanoic acid and solvent may be recovered and recycled.

In the productions of the ester of the present invention and the isotridecanoic acid, a product obtained in each stage may be purified as necessary by a method normally used in organic synthetic chemistry (such as washing with water and/or an alkaline aqueous solution, treatment with activated carbon, an adsorbent, or the like, various chromatographic methods, distillation).

The ester of the present invention has excellent properties such as low-temperature fluidity, oxidation stability, and low volatility, as well as sufficient properties such as lubricity, viscosity-temperature characteristic, electrical insulating properties, hydrolysis stability, and biodegradability, which are required for industrial lubricants and the like. Moreover, the ester of the present invention is excellent also in miscibility with a natural refrigerant, lubricity in the presence of a natural refrigerant, refrigerant-solution viscosity in the presence of a natural refrigerant, and so forth, which are required for refrigerating machine oils for natural refrigerants.

In the present invention, the terms kinematic viscosity and viscosity index refer to values measured according to the method of JIS K2283:2000 using a Cannon-Fenske viscometer. The ester of the present invention has a kinematic viscosity at 40° C. within the range of 80 to 140 mm$^2$/s, preferably within a range of 90 to 135 mm$^2$/s from the viewpoints of retaining the oil film, energy saving, and so forth. Meanwhile, the term viscosity index refers to a viscosity-temperature characteristic, and it can be said that the higher the viscosity index, the more favorable the viscosity-temperature characteristic. The viscosity index of the ester of the present invention is not particularly limited, but is preferably 90 or more from the viewpoints of retaining the oil film, energy saving, and so forth.

The term low-temperature fluidity refers to a viscosity characteristic in a low-temperature range, and is indicated by pour point, freezing point, channel point, or the like. The ester of the present invention preferably has a pour point of −40° C. or less. A lubricant having a low pour point is preferable in that, for example, an operation failure does not occur in an apparatus using the lubricant because the fluidity does not deteriorate even in winter or low temperature environments such as a cold region. Note that, in the present invention, a pour point means a pour point measured according to the method of JIS K2269:1987.

The oxidation stability can be evaluated, for example, by conducting an oxidation stability test according to the method of JIS K2514:1996. A lubricant having a high oxidation stability is preferable in that the lubricant deteriorates less even in the presence of oxygen, so that the properties of the lubricant can be maintained after the long-term use.

The evaporation can be evaluated, for example, with reference to the method of JIS C2101:1999, by measuring an evaporation loss by heating after a sample is exposed to high temperature for a long time. A lubricant having a low evaporation is preferable in that the evaporation loss by heating the lubricant is small even in use environments in a high-temperature range such as an engine, so that an operation failure does not occur in an apparatus using the lubricant, and that an environmental problem due to a deterioration in exhaust gas properties does not occur, for example.

Examples of the lubricity include friction-reducing properties, wear-reducing properties (anti-wear properties), extreme pressure properties, and the like. The lubricity can be evaluated with friction and wear testing machines such as a shell four-ball friction tester with reference to ASTM D4172, ASTM D2783, and so forth. A lubricant having a high lubricity is preferable in view of energy saving, extending an apparatus lifetime, and so forth attributable to reductions in the wear resistance between machine elements and in the wear loss of a sliding member. When a lubricant is used as refrigerating machine oil, the lubricant is required to have also a lubricity in the presence of a refrigerant. The lubricity in the presence of a refrigerant can be evaluated, for example, with friction and wear testing machines such as a block-on-ring friction and wear testing machine (manufactured by FALEX Corporation) of a sealed pressurization type according to ASTM D2714, and a Pin & Vee Block friction and wear testing machine (manufactured by FALEX Corporation) of a sealed pressurization type according to ASTM D2670.

Moreover, the lubricity is related to the viscosity of a lubricant in retaining the oil film necessary for the lubrication. Particularly, when a lubricant is used as a refrigerating machine oil, a refrigerant dissolves in the refrigerating machine oil in a refrigerant circulation cycle, so that the viscosity (refrigerant-solution viscosity) of a fluid composition, which is the mixture of the refrigerating machine oil and the refrigerant, may decrease, and may possibly result in a problem of a lubrication failure. For these reasons, a high refrigerant-solution viscosity is required. The refrigerant-solution viscosity can be determined, for example, by sealing a refrigerant and a refrigerating machine oil in a pressure-resistant vessel, stabilizing the pressure of a gas phase portion and the temperature in the vessel in predetermined states, and then measuring the viscosity of a liquid phase portion by using an in-line viscometer or the like. Incidentally, as one of the methods for improving the lubricity, increasing the viscosity of the refrigerating machine oil is conceivable. However, this method is not desirable from the viewpoint of energy saving. A mixture of propane and an ester 3 (Example 3 to be described later), which is one embodiment of the ester of the present invention, was excellent in refrigerant-solution viscosity (temperature: 60° C., absolute pressure: 1.6 MPa) being 2.3 cP.

The term electrical insulating properties are indicated by volume resistivity, and the properties are measured according to the method of JIS C2101:1999. A lubricant having high electrical insulating properties is preferable in that, for example, such a lubricant is capable of preventing electrolytic corrosion in a motor and the like which are used in the lubricant. The volume resistivity of the ester of the present invention is not particularly limited, but the volume resistivity at 30° C. is preferably $1.0 \times 10^{13}$ Ω·cm or more, more preferably $1.0 \times 10^{14}$ Ω·cm or more, and furthermore preferably $1.0 \times 10^{15}$ Ω·cm or more.

The hydrolysis stability can be evaluated, for example, by storing a test oil in the presence of water for a certain time, and then measuring an increased value(s) of the acid number and/or hydroxyl number. In this event, the test may be accelerated by heating or adding an acid or an alkali. A lubricant having a high hydrolysis stability is preferable in that, for example, the lubricant does not deteriorate much even in a use environment with a humid air atmosphere, so that an operation failure does not occur in an apparatus using the lubricant.

The acid number of the ester of the present invention is not particularly limited, but is preferably 0.1 mgKOH/g or less, and more preferably 0.05 mgKOH/g or less. If a lubricant has a high acid number, this promotes the degradation of the lubricant and causes metal corrosion and so on. For these reasons, a low acid number is required. Note that, in the present invention, the term acid number means an acid number measured according to the method of JIS K2501.

In the case where the ester of the present invention is used as a refrigerating machine oil, the refrigerating machine oil is required to have an excellent miscibility with a refrigerant (refrigerant miscibility). If the refrigerant miscibility is poor, the refrigerant and the refrigerating machine oil are phase-separated, and the refrigerating machine oil discharged from a refrigerant compressor builds up in a refrigerant circulation cycle, which may possibly result in problems of a lubrication failure and the like in the refrigerant compressor. The refrigerant miscibility is generally indicated by using two-phase separation temperature. It can be said that the lower the two-phase separation temperature, the more favorable the miscibility at lower temperature. The two-phase separation temperature of a mixture of a refrigerant and the ester of the present invention is preferably −40° C. or less, provided that the content of the ester of the present invention is 20% by mass. Note that, in the present invention, the two-phase separation temperature means a value measured according to the method of JIS K2211:2009.

The ester of the present invention can be used in industrial lubricants, grease compositions, and the like. In this respect, examples of the industrial lubricants include automotive lubricants, machine oils used for industrial machineries, metalworking oils used for metalworking, and the like. The automotive lubricants specifically include an engine oil, a gear oil, a transmission oil, and a motor oil utilized for a hybrid vehicle or an electric vehicle, and other similar oils. The machine oils specifically include a refrigerating machine oil, a turbine oil, a gear oil (but not for automobiles), a hydraulic oil, and the like. The metalworking oils specifically include a cutting oil, a rolling oil, a rust preventive oil, and the like. Meanwhile, examples of the grease compositions include grease compositions used for parts (such as rolling bearing, ball bearing, linear guide, ball joint, universal joint, gear) incorporated in automobiles, industrial machineries, machine tools and the like, and other similar compositions.

Here, in the case where the ester of the present invention is used as a refrigerating machine oil, a natural refrigerant can be suitably used as the refrigerant. The natural refrigerant includes propane (R290), butane (R600), isobutane (R600a), ammonia (R717), carbon dioxide (R744), and the like. From the viewpoints of the lubricity in the presence of a refrigerant and the refrigerant miscibility of the ester of the present invention, propane, butane, or isobutane is preferable.

EXAMPLES

Hereinafter, the present invention will be described more specifically by way of Production Examples, Examples, Comparative Examples, and Test Examples. However, the present invention is not limited to Examples below.

Nuclear magnetic resonance spectra were measured with the following measurement instrument under the following measurement conditions.

[$^1$H-NMR]
Measurement instrument; JNM-ECA500 (500 MHz) manufactured by JEOL Ltd.
Measurement conditions;
Measurement method; $^1$H-NMR
Standard substance; tetramethylsilane (TMS)
Solvent; $CDCl_3$
Sample concentration; 40% by mass
Number of scans; 64
Chemical shift reference; TMS=0 ppm
[$^{13}$C-NMR]
Measurement instrument; JNM-ECA500 (500 MHz) manufactured by JEOL Ltd.
Measurement conditions;
Measurement method; $^{13}$C-NMR (the inverse gated decoupling technique, the DEPT technique)
Solvent; $CDCl_3$
Sample concentration; 40% by mass
Number of scans; 1000 (the inverse gated decoupling technique), 10000 (the DEPT technique)
Chemical shift reference; $CDCl_3$=77 ppm Production Examples of isotridecanoic acids A to E used in Examples and isotridecanoic acids F and G used in Comparative Examples will be described below. In addition, n-tridecanoic acid used in Comparative Example was tridecanoic acid (product name) commercially available from Tokyo Chemical Industry Co., Ltd.

Production Example 1

[Production of Isotridecanoic Acid A]

Butene (a mixture of 1-butene, 2-butene, and isobutene; provided that the isobutene content was less than 10% by mass of the whole) was reacted at 200° C. at 5 MPa using a solid phosphoric acid catalyst with diatomaceous earth as a support. Then, the product was purified by distillation. Thereby, a butene trimer (initial boiling point: 192° C., dry point: 202° C.) was obtained. The obtained butene trimer was hydroformylated under conditions of a pressure at 16 MPa and a temperature at 150° C. in the presence of a gas mixture of hydrogen and carbon monoxide (hydrogen/carbon monoxide mixing ratio (molar ratio); 1.1/1) using, as a catalyst, hydridotetracarbonylcobalt having been formed by treating cobalt hydroxide with a gas mixture of hydrogen and carbon monoxide. After the catalyst was removed, the resultant was oxidized and subsequently purified by distillation (recovered temperature: 170 to 175° C., reduced pressure: 5 Torr). Thus, isotridecanoic acid A was obtained.

Production Example 2

[Production of Isotridecanoic Acid B]

Isotridecanoic acid B was obtained in the same manner as in Example 1, except that the hydroformylation was performed under conditions of a pressure at 5 MPa and a temperature at 150° C. in the presence of a gas mixture of hydrogen and carbon monoxide (hydrogen/carbon monoxide mixing ratio (molar ratio); 1.3/1) using, as a catalyst, (acetylacetonato)dicarbonylrhodium to which tris(2,4-di-t-butylphenyl)phosphite had been added, and that the isotridecanoic acid was purified by distillation under conditions of a recovered temperature at 165 to 175° C. and a reduced pressure at 5 Torr.

Production Example 3

[Production of Isotridecanoic Acid C]

Isotridecanoic acid C was obtained in the same manner as in Example 1, except that the isotridecanoic acid was purified by distillation under conditions of a recovered temperature at 165 to 175° C. and a reduced pressure at 5 Torr.

Production Example 4

[Production of Isotridecanoic Acid D]

Butene (a mixture of 1-butene, 2-butene, and isobutene; provided that the isobutene content was less than 10% by mass of the whole) was reacted at 45° C. at 1 MPa using, as catalysts, nickel octanoate, dichloroethylaluminum, and ethylene glycol (molar ratio: nickel octanoate/dichloroethylaluminum/ethylene glycol=1/15/1). Then, the product was purified by distillation. Thereby, a butene trimer (initial boiling point: 192° C., dry point: 202° C.) was obtained. The obtained butene trimer was subjected to hydroformylation, catalyst removal, oxidization, and distillation purification (recovered temperature: 165 to 175° C., reduced pressure: 5 Torr) by the same processes as in Production Example 1. Thus, isotridecanoic acid D was obtained.

Production Example 5

[Production of Isotridecanoic Acid E]

Isotridecanoic acid E was obtained in the same manner as in Example 1, except that the isotridecanoic acid was purified by distillation under conditions of a recovered temperature at 165 to 167° C. and a reduced pressure of 5 Torr.

Production Example 6

[Production of Isotridecanoic Acid F]

Propylene was reacted at 200° C. at 5 MPa using a solid phosphoric acid catalyst with diatomaceous earth as a support. Then, the product was purified by distillation. Thereby, a propylene tetramer was obtained. The obtained propylene tetramer was subjected to hydroformylation, catalyst removal, oxidization, and distillation purification (recovered temperature: 154 to 169° C., reduced pressure: 5 Torr) by the same processes as in Production Example 1. Thus, isotridecanoic acid F was obtained.

Production Example 7

[Production of Isotridecanoic Acid G]

Isobutene was reacted at 200° C. at 5 MPa using a solid phosphoric acid catalyst with diatomaceous earth as a support. Then, the product was purified by distillation. Thereby, an isobutene trimer was obtained. The obtained isobutene trimer was subjected to hydroformylation, catalyst removal, oxidization, and distillation purification (recovered temperature: 147° C., reduced pressure: 5 Torr) by the same processes as in Production Example 1. Thus, isotridecanoic acid G was obtained.

Table 1 shows the structural information on the isotridecanoic acids A to G and n-tridecanoic acid analyzed from the nuclear magnetic resonance spectra.

bling. After the reaction, the reaction product was stirred under a reduced pressure of 0.4 kPa at 223 to 229° C. for 4 hours. Thereby, the unreacted carboxylic acid in the reaction product was distilled off. The reaction product was washed at 80° C. for 0.5 hours with 90 g of an alkaline aqueous solution containing sodium hydroxide in an amount 2 times larger in terms of moles than the acid number of the reaction product. Thereafter, the reaction product was washed with 100 g of water at 90° C. for 0.3 hours three times. After that, the reaction product was stirred with nitrogen bubbling under a reduced pressure of 0.6 kPa at 100° C. for 1 hour to dry the reaction product.

To the reaction product, 3.5 g of an adsorbent (manufactured by Kyowa Chemical Industry Co., Ltd., product name; KYOWAAD 500) and 1.8 g of activated carbon (manufactured by Japan EnviroChemicals, Limited, product name; SHIRASAGI P) were added. With nitrogen bubbling, the reaction product was stirred under a reduced pressure of 0.6 kPa at 100° C. for 2 hours. Then, the reaction product was filtered in a nitrogen atmosphere by using a filter aid (manufactured by Showa Chemical Industry Co., LTD., product name; RADIOLITE #500) having been dried under reduced pressure in advance. Thus, 312 g of an ester 1 was obtained.

Example 2

[Production of Ester of Isotridecanoic Acid B and Pentaerythritol (Ester 2)]

An ester 2 was obtained in the same manner as in Example 1, except that the isotridecanoic acid B was used instead of the isotridecanoic acid A, and that the molar ratio between the amounts of pentaerythritol and the isotridecanoic acid B used was set to 1/4.8 (pentaerythritol/the isotridecanoic acid B).

TABLE 1

|  | Isotridecanoic acid A | Isotridecanoic acid B | Isotridecanoic acid C | Isotridecanoic acid D | Isotridecanoic acid E | Isotridecanoic acid F | Isotridecanoic acid G | n-Tridecanoic acid |
|---|---|---|---|---|---|---|---|---|
| Number of terminal methyl groups per molecule | 2.6 | 2.7 | 2.9 | 3.0 | 3.3 | 3.9 | 6.0 | 1.0 |
| Proportion of tertiary carbon atoms in total constituent carbon atoms [% by mass] | 10.1 | 13.8 | 12.6 | 12.7 | 15.1 | 5.8 | 7.5 | 0 |
| Proportion of branching at α carbon [% by mass] | 12 | 56 | 24 | 17 | 45 | 11 | 0 | 0 |

Example 1

[Production of Ester of Isotridecanoic Acid A and Pentaerythritol (Ester 1)]

Into a reactor equipped with a Dean-Stark trap, 52 g of pentaerythritol (0.38 mol, manufactured by Koei Perstorp Co., Ltd., product name; Pentarit-S) and 393 g (1.8 mol) of the isotridecanoic acid A were introduced and mixed together. While the mixture was being stirred, the pressure was reduced to 80 kPa. Then, the pressure was returned to atmospheric pressure with nitrogen. This operation was performed three times. Thereby, the air inside the reactor was replaced with nitrogen.

Subsequently, the mixture was stirred at 180 to 232° C. for 14 hours under atmospheric pressure with nitrogen bub- Example 3

[Production of Ester of Isotridecanoic Acid C and Pentaerythritol (Ester 3)]

An ester 3 was obtained in the same manner as in Example 1, except that the isotridecanoic acid C was used instead of the isotridecanoic acid A, and that the molar ratio between the amounts of pentaerythritol and the isotridecanoic acid C used was set to 1/4.8 (pentaerythritol/the isotridecanoic acid C).

Example 4

[Production of Ester of Isotridecanoic Acid D and Pentaerythritol (Ester 4)]

An ester 4 was obtained in the same manner as in Example 1, except that the isotridecanoic acid D was used instead of the isotridecanoic acid A, and that the molar ratio between the amounts of pentaerythritol and the isotridecanoic acid D used was set to 1/4.8 (pentaerythritol/the isotridecanoic acid D).

Example 5

[Production of Ester of Isotridecanoic Acid E and Pentaerythritol (Ester 5)]

An ester 5 was obtained in the same manner as in Example 1, except that the isotridecanoic acid E was used instead of the isotridecanoic acid A, and that the molar ratio between the amounts of pentaerythritol and the isotridecanoic acid E used was set to 1/4.8 (pentaerythritol/the isotridecanoic acid E).

Comparative Example 1

[Production of Ester of Isotridecanoic Acid F and Pentaerythritol (Ester 6)]

An ester 6 was obtained in the same manner as in Example 1, except that the isotridecanoic acid F was used instead of the isotridecanoic acid A, and that the molar ratio between the amounts of pentaerythritol and the isotridecanoic acid F used was set to 1/4.8 (pentaerythritol/the isotridecanoic acid F).

Comparative Example 2

[Production of Ester of Isotridecanoic Acid G and Pentaerythritol (Ester 7)]

An ester 7 was obtained in the same manner as in Example 1, except that the isotridecanoic acid G was used instead of the isotridecanoic acid A, and that the molar ratio between the amounts of pentaerythritol and the isotridecanoic acid G used was set to 1/4.8 (pentaerythritol/the isotridecanoic acid G). Note that the ester 7 was a solid at room temperature (melting point; 98 to 100° C.), and hence cannot be used as an industrial lubricant.

Comparative Example 3

[Production of Ester of n-Tridecanoic Acid and Pentaerythritol (Ester 8)]

An ester 8 was obtained in the same manner as in Example 1, except that n-tridecanoic acid was used instead of the isotridecanoic acid A, and that the molar ratio between the amounts of pentaerythritol and n-tridecanoic acid used was set to 1/4.8 (pentaerythritol/n-tridecanoic acid). Note that the ester 8 was a solid at room temperature (melting point; 53 to 54° C.), and hence cannot be used as an industrial lubricant.

(Test Example 1) Measurement of Acid Number

The esters 1 to 8 were measured for the acid number according to the indicator titration method of JIS K2501. Table 2 shows the result.

(Test Example 2) Measurement of Kinematic Viscosity

The esters 1 to 6 were measured for the kinematic viscosity at 40° C. and 100° C. according to the method of JIS K2283:2000 using a Cannon-Fenske viscometer. Moreover, the viscosity indexes were calculated according to this method. Table 2 shows the results.

(Test Example 3) Measurement of Pour Point

The esters 1 to 6 were measured for the pour point according to the method of JIS K2269:1987 using an automatic pour point tester RPC-01CML (manufactured by Rigo Co., Ltd.). Table 2 shows the result.

(Test Example 4) Measurement of RBOT Life (Evaluation of Oxidation Stability)

The esters 1 to 6 were subjected to an oxidation stability test using a rotating bomb oxidation stability tester RBOT-02 (manufactured by Rigo Co., Ltd.) according to the method of JIS K2514:1996, except that no water was added. Specifically, 50 g of one of the esters 1 to 6 and an electrolytic copper wire (diameter: 1.6 mm, length: 3 m) which had been polished with sandpaper #400 were placed in a pressure-resistant vessel. Then, oxygen was introduced into the pressure-resistant vessel until the pressure reached 620 kPa. The pressure-resistant vessel was placed in a thermostat bath at 150° C. and rotated at 100 rpm to start the test. This time point was recorded as a test starting point. A point when the pressure of the pressure-resistant vessel dropped by 175 kPa after the pressure reached the maximum was determined as an end point to obtain a period from the test starting point to the end point (RBOT life). Table 2 shows the result. It can be said that if the RBOT life is 1000 seconds or more, the oxidation stability is excellent. A further longer RBOT life indicates that the ester has a more excellent oxidation stability.

(Test Example 5) Measurement of Evaporation Loss by Heating (Evaluation of Evaporation)

Each of the esters 1 to 6 was subjected to an evaporation test. Specifically, 3 g of one of the esters 1 to 6 was placed in a glass Petri dish (inner diameter: 75 mm), and heated in a thermostat bath at 120° C. for 48 hours. A change in the mass of the ester between before and after the heating was measured to obtain an evaporation loss by heating according to the following formula 4. Table 2 shows the result. A smaller evaporation loss by heating indicates that the ester is suitable for use in a high-temperature range.

Evaporation loss by heating [% by mass]=100×(mass before heating (g)−mass after heating (g))/mass before heating (g)  (formula 4)

(Test Example 6) Measurement of Wear Scar Diameter (Evaluation of Lubricity)

Each of the esters 1 to 6 was measured for the wear scar diameter using a shell four-ball friction tester (manufactured by Shinko Engineering Co., Ltd.). A test was conducted under conditions of load: 200 N, rotating speed: 600 rpm, time: 60 minutes, temperature: 80° C., and test material: [test balls (SUJ-2)]. After the test, the wear scar diameter was measured. An average value of three stationary balls in all the vertical direction and the horizontal direction was regarded as the wear scar diameter. Table 2 shows the result. A smaller value of the wear scar diameter indicates that the lubricity (anti-wear properties) is more excellent when the ester is used as a lubricant.

(Test Example 7) Measurement of Volume Resistivity (Evaluation of Electrical Insulating Properties)

The esters 1 to 5 were measured for the volume resistivity at 30° C. according to the method of JIS C2101:1999 using a digital ultra-high resistance/micro current meter R8340A (manufactured by ADVANTEST CORPORATION) and a liquid electrode DAC-OBE-2 (manufactured by Soken Electric Co., Ltd.). The result is shown below.

(Test Example 8) Evaluation of Miscibility with Propane Refrigerant

A mixture of 0.3 g of one of the esters 1 to 5 and 1.2 g of a propane refrigerant (manufactured by Iwatani Industrial Gases Corporation, product name; ECO FREEZE 290) were sealed in a pressure-resistant glass tube. The miscibility at −40° C. was observed according to the method of JIS K2211:2009, and evaluated at three levels of "miscible", "cloudy", and "separated". Here, "miscible" indicates a state where the mixture is in a homogeneous phase and is transparent as a whole, "cloudy" indicates a state where the entire mixture turns white and cloudy, and "separated" indicates a state where the mixture was separated into two layers with an interface. The result is shown below.

TABLE 2

|  | Example 1 | Example 2 | Example 3 | Example 4 | Example 5 | Comparative Example 1 | Comparative Example 2 | Comparative Example 3 |
|---|---|---|---|---|---|---|---|---|
| Ester | Ester 1 | Ester 2 | Ester 3 | Ester 4 | Ester 5 | Ester 6 | Ester 7 | Ester 8 |
| Acid Number [mgKOH/g] | 0.008 | 0.002 | 0.003 | 0.008 | 0.008 | 0.009 | 0.014 | 0.008 |
| Kinematic viscosity 40° C. [mm²/s] | 90.8 | 95.1 | 99.1 | 112.6 | 134.8 | 197.2 | —*¹ | —*¹ |
| 100° C. [mm²/s] | 12.0 | 11.5 | 12.0 | 12.7 | 13.3 | 16.3 |  |  |
| Viscosity index | 124 | 109 | 112 | 105 | 92 | 84 |  |  |
| Pour point [° C.] | −52.5 | −47.5 | −52.5 | −47.5 | −45.0 | −35.0 |  |  |
| RBOT life [s] | 1100 | 1420 | 1400 | 1260 | 1220 | 1120 |  |  |
| Evaporation loss by heating [% by mass] | 3.0 | 2.4 | 2.0 | 2.4 | 3.1 | 9.2 |  |  |
| Wear scar diameter [mm] | 0.57 | 0.61 | 0.59 | 0.61 | 0.61 | 0.61 |  |  |

*¹Since the esters 7 and 8 were solids at room temperature, no test was conducted.

From Table 2, the esters 1 to 5 of the present invention had kinematic viscosities of 90.8 to 134.8 mm²/s, viscosity indexes of 92 to 124, pour points of −52.5 to −45.0° C., RBOT lives of 1100 to 1420 seconds, and evaporation losses by heating of 2.0 to 3.1% by mass. It can be seen that the esters 1 to 5 of the present invention are excellent in low-temperature fluidity and oxidation stability, and are superior in low volatility. In contrast, it can be seen that the ester 6, which is not the present invention, has a higher pour point and a larger evaporation loss by heating than the esters 1 to 5 of the present invention. Additionally, the esters 7 and 8 are solids at room temperature, and it can be said that it is difficult to use the esters 7 and 8 in industrial lubricants and the like.

In Test Example 6, the esters 1 to 5 of the present invention had wear scar diameters of 0.57 to 0.61 mm, and the ester 6 had a wear scar diameter of 0.61 mm. It can be seen that the esters of the present invention have sufficient lubricities.

In Test Example 7, the esters 1 to 5 had volume resistivities (30° C.) of $1\times10^{15}$ Ω·cm or more. It can be seen that the esters of the present invention have sufficient electrical insulating properties.

In Test Example 8, the solution state of any of the esters 1 to 5 with the propane refrigerant was "miscible". It can be seen that the esters of the present invention have sufficient miscibilities with a propane refrigerant.

The present invention makes it possible to provide an ester of pentaerythritol and so forth used in industrial lubricants and the like having excellent properties such as low-temperature fluidity, oxidation stability, and low volatility.

The invention claimed is:

1. An ester of pentaerythritol with isotridecanoic acid, wherein
  (i) the ester of pentaerythritol has a kinematic viscosity at 40° C. within a range of 80 mm²/s to 140 mm²/s, and
  (ii) a number of terminal methyl groups per isotridecanoic acid molecule in the isotridecanoic acid determined by $^1$H-NMR measurement is within a range of 2.6 to 3.4 on average.

2. The ester of pentaerythritol according to claim 1, wherein a proportion of tertiary carbon atoms in total constituent carbon atoms of the isotridecanoic acid determined by $^{13}$C-NMR measurement is within a range of more than 10% by mass to 20% by mass or less.

3. The ester of pentaerythritol according to claim 1, wherein the isotridecanoic acid is isotridecanoic acid derived from a product obtained by hydroformylating a butene trimer in the presence of a cobalt catalyst and a gas mixture of hydrogen and carbon monoxide.

4. The ester of pentaerythritol according to claim 1, wherein the isotridecanoic acid is isotridecanoic acid derived from a product obtained by hydroformylating a butene trimer in the presence of a rhodium catalyst and a gas mixture of hydrogen and carbon monoxide.

5. Isotridecanoic acid wherein
  a number of terminal methyl groups per molecule of the acid determined by $^1$H-NMR measurement is within a range of 2.6 to 3.4 on average,
  a proportion of tertiary carbon atoms in total constituent carbon atoms of the acid determined by $^{13}$C-NMR measurement is within a range of more than 10% by mass to 20% by mass or less, and
  a proportion of branching at an α carbon of the isotridecanoic acid is within a range of 15% by mass to 70% by mass.

6. The ester of pentaerythritol according to claim 2, wherein the isotridecanoic acid is isotridecanoic acid derived from a product obtained by hydroformylating a butene trimer in the presence of a cobalt catalyst and a gas mixture of hydrogen and carbon monoxide.

7. The ester of pentaerythritol according to claim 2, wherein the isotridecanoic acid is isotridecanoic acid derived from a product obtained by hydroformylating a butene trimer in the presence of a rhodium catalyst and a gas mixture of hydrogen and carbon monoxide.

* * * * *